United States Patent [19]

Visuri et al.

[11] Patent Number: 5,330,621
[45] Date of Patent: Jul. 19, 1994

[54] CONTINUOUS ELEMENTAL ANALYSIS OF PROCESS FLOWS

[75] Inventors: Pertti Visuri, San Diego, Calif.; Erkki Kiiskila, Karhula, Finland; Markku Koskelo, Middletown, Conn.

[73] Assignee: A. Ahlstrom Corporation, Noormarkku, Finland

[21] Appl. No.: 948,645

[22] Filed: Sep. 23, 1992

[51] Int. Cl.$^5$ .............................................. D21C 7/12
[52] U.S. Cl. ....................................... 162/49; 162/198; 162/DIG. 10; 250/472.1; 376/159; 436/173; 436/55
[58] Field of Search ............... 162/0.49, 198, DIG. 10; 376/159; 250/472; 436/173, 94, 55

[56] References Cited

U.S. PATENT DOCUMENTS

| | | | |
|---|---|---|---|
| 3,858,111 | 12/1974 | Simpson | 324/0.5 R |
| 3,966,973 | 6/1976 | Henry et al. | 426/231 |
| 4,190,768 | 2/1980 | Arnold et al. | 376/159 |
| 4,340,443 | 7/1982 | Clayton et al. | 376/342 |
| 4,388,530 | 6/1983 | Lubecki et al. | 378/45 |
| 4,390,957 | 6/1983 | Skarlos et al. | 364/550 |
| 5,133,901 | 7/1992 | Peterson et al. | 252/626 |

FOREIGN PATENT DOCUMENTS

WO9117305 11/1991 PCT Int'l Appl. ................... 162/47

OTHER PUBLICATIONS

Wormald et al. "In-situ Analysis of Coal by Measurement of Neutron-Induced Prompt γ-rays", Nuclear Geophysics (C. G. Clayton Ed.), Pergamon Press, GB., 1983; pp. 71-82.

Faix et al, "Continuous Process Control of Pulping by FTIR Spect", 1989 Wood and Pulping chemistry, pp. 1-8.

Cho et al. "Sugar Content Measurement in Fruit Tissue Using Water Peak Suppression in High Resolution H-MR", Journal of Food Science, vol. 56, No. 4, 1991 pp. 1091-1094.

Pearson et al., "Industrial Magnetic Resonance (IMR) A Magnetic Resonance Spectrometer built as an Industrial Process Controller", 28th Exp. Nuclear Magnetic Resonance Spec Conferences, Apr. 2-6, 1989.

Pulp & Paper Canada 90:1, Chip Handing, "Chip moisture and bulk density measurement systems: Calibration and operation", Javid et al, pp. 87-93.

Nuclear Instruments and Methods 160 (1979) 173-182, North-Holland Publishing Co., "Measurement of Specific Energy, Ash and Moisture in Bulk Coal Samples by a Combined Neutron and Gamma-Ray Method", Sowerby, pp. 173-182.

Journal of Radioanalytical Chemistry, vol. 71, No. 1-2 (1982)253-264, "On-Line Analysis of Coal by Neutron Induced Gamma Spectrometry", Wilde et al.

(List continued on next page.)

*Primary Examiner*—Peter Chin
*Assistant Examiner*—Dean T. Nguyen
*Attorney, Agent, or Firm*—Nixon & Vanderhye

[57] ABSTRACT

A method and apparatus are provided for analyzing the elemental constituents of fluid streams in the cellulose pulp industry, such as liquid with dissolved solids for treatment of cellulose pulp or from the treatment of cellulose pulp, or liquid slurries including comminuted cellulose material. Continuous on-line elemental analyses are made of one or more such fluid streams, and at least the partial elemental make-up (either material, or of elements added for marking) of the streams determined. Then one or more processes for acting on the fluid streams are controlled to optimize the processes as a result of the analyses made. The invention is particularly useful in the continuous on-line analysis of black liquor utilizing prompt gamma neutron activation analysis, and controlling the operation of an evaporator or recovery boiler. The invention is also applicable to a paper pulp slurry in which case the carbon content of the slurry is analyzed to determine the precise solids consistency, and may employ NMR or 'H-MR.

25 Claims, 4 Drawing Sheets

OTHER PUBLICATIONS

Proceedings of an International Symposium on Nuclear Techniques in the Exploration and Exploitation of Energy and Mineral Resources Organized by The International Atomic Energy Agency and Held in Vienna, Jun. 5–8, 1990, On–Line Bulk Analysis of Raw Material in a Cement Plant Using the Neutron Irradiation and Capture Gamma Ray Technique, Baron et al, pp. 569–583.

Ageng 1992 International Conference on Agricultural Engineering, Uppsala, Sweden, Jun. 1, 1992, "Prototype of Non–Destructive Fruit Sweetness Sensor", Stroshine et al, cover and pp. 1–6.

American Society of Electrical Engineers, Paper No. 91–7554, Dec. 17–21, 1991, "FEM Solenoid Probe Coil for a Magnetic Resonance Fruit Sweetness Sensor", Wai et al, pp. 1–8.

American Society of Agricultural Engineers, Paper No. 91–7511, 1991 ASAE Winter Meeting, "Expert System for Water Peak Suppression in Pulsed Proton Magnetic Resonance", Cho et al, cover and pp. 1–6.

Food Control, Jan. 1992, Ripeness sensor development based on nuclear magnetic resonance, Bellon et al, pp. 45–48.

American Society of Agricultural Engineers, vol. 33(4): Jul.–Aug. 1990, "Magnet Console of a NMR–Based Sensor to Detect Ripeness of Fruit", Cho et al, pp. 1043–1050.

Journal of Feed Science, vol. 56, No. 4, 1991, "Sugar Content Measurement in Fruit Tissue Using Water Peak Suppression in High Resolution $^1$H Magnetic Resonance", Cho et al, pp. 1091–1094.

American Society of Agricultural Engineers, Paper No. 91–3524, 1991 ASAE Winter Meeting, "Prototype of Non–Destructive Fruit Sweetness Sensor" Cho et al, 12 pages.

CONTINUOUS ELEMENTAL ANALYSIS OF PROCESS FLOWS

BACKGROUND AND SUMMARY OF THE INVENTION

In the production of cellulose pulp, pulp production processes, and chemical recovery processes are typically designed so that control is accomplished by obtaining empirical data ultimately used to control the processes, or by sacrificing process optimization in order to utilize simple equipment. While some pulp processes do utilize continuous monitoring of slurry qualities in controlling pulp treatment based upon such an analysis, these typically are performed utilizing density measurements. For example in U.S. Pat. No. 4,239,590 a method of maintaining uniformity of the cellulose material fed to a continuous digester is practiced by using gamma absorption techniques to determine the density of the chips slurry just prior to introduction into the digester, and then subsequent to treatment. In co-pending application Ser. No. 07/782,828 filed Oct. 25, 1991, now U.S. Pat. No. 5,266,159, the feed of cellulose material to a continuous digester is controlled by continuously determining a quality related to mass flow of the material being fed by passing a stream of nuclear particles through the flow of material to determine its density, utilizing a feed chute, and a chips meter. However, most processes do not utilize continuous monitoring techniques because they have not heretofore provided information that is highly useful in effecting subsequent controls of process conditions and equipment.

There are some systems (e.g. "The Drywood System") that have been marketed for the pulp and paper industry that utilize neutron radiation for measurement of the water content in the incoming wood chip flow. These are based on the principal of measuring the total quantity of the wood chip inflow on a conveyor belt by utilizing conventional gamma ray measurements to calculate the mass of the chips on the conveyor based on attenuation of the gamma rays when they pass through the conveyed material. In addition to this measurement, the same flow of wood chips is irradiated with fast neutrons. The back scattered or penetrated neutron spectrum is measured. Since the fast neutrons quickly slow down in any material containing light nuclei, the neutron energy spectrum shifts to lower energies. In other words the neutrons thermalize in the media. The efficiency of thermalization is dependent on the proportions of nuclei with different masses in the media where the thermalization is taking place. Based on this phenomena, it is possible to find the ratio of hydrogen atoms to heavier carbon and oxygen atoms in the flow of wood chips, which is being irradiated in this measurement system. The system works reasonably well with water contents from about 20–60%, but becomes very inaccurate as the water content increases. While this measurement does utilize both gamma radiation and neutron radiation, it does not measure elemental composition and is based on observing neutron thermalization and gamma attenuation only.

According to the present invention a method and apparatus are provided for continuously analyzing fluid streams associated with the production of cellulose pulp, and for effecting process control of equipment as a result of such analysis. According to the invention, continuous on-line elemental analyses are made. The fluid streams may be conventional streams, or specifically "marked" to facilitate analysis. By determining what amount of various chemical constituents of a fluid stream, various controls can be implemented.

The invention is particularly useful in analyzing black liquor, which contains dissolved solids, including lignin, as a result of digestion of cellulose, but the invention is also useful for analyzing slurries containing comminuted cellulose material. While continuous on-line elemental analysis has heretofore been known in a number of industries, such as in the coal, oil, cement, and mining industries, such as for determining the ash content of coal, or the elemental analysis of cement, or the amount of silica in coal for a gasifier installation, utilizing the conventional equipment (such as manufactured by Science Applications International Corporation, MDH-Motherwell Inc., and Gamma-Metrics), such techniques have not heretofore been applied to the pulp and paper industry.

One reason elemental analysis techniques have not been applied to the pulp and paper industry undoubtedly is because many of the prior art techniques are applied to solid materials, rather than liquids, and solid materials are much easier to analyze. Regardless of the reasons why such techniques have not been applied in the pulp and paper industry heretofore, however, it has been found according to the invention that such techniques can be very beneficial for a number of pulp applications, and can clearly justify the continuous on-line monitoring equipment necessary to practice such techniques.

According to one basic aspect of the present invention, a method for effecting process control of equipment used for the production of cellulose pulp is provided. The method comprises the following steps: (a) Making continuous on-line elemental analyzes of one or more fluid streams comprising liquid with dissolved solids for treatment of cellulose pulp or from the treatment of cellulose pulp, or liquid slurries including comminuted cellulose material. (b) Determining at least the partial elemental makeup of the one or more fluid streams. And, (c) in response to (b), controlling (either automatically or manually) one or more processes for acting on the one or more fluid streams to optimize the one or more processes.

Step (a) is preferably practiced by bombarding the fluid stream being analyzed with radioactive particles or radiation, and detecting radioactive particles or radiation as a result of that bombardment. One particularly preferred technique is prompt gamma neutron activation analysis, although other techniques such as nuclear magnetic resonance (NMR) (and in particular proton magnetic resonance ('H-MR), proton activation analysis, and X-ray fluorescence, can be utilized. In the case of NMR or 'H-MR, there will be additional benefits of determining the concentrations of various molecules or chemical substances in the process flow in addition to the elemental composition. In addition, it may be possible to determine the distribution of the various substances in the process flow, for example, to find out whether the flow is homogenous and whether the chemicals are bound to pulp fibers or flowing freely in the aqueous part of the slurry. There may also be the further step (d), prior to step (a), of adding a marking chemical (e.g. chlorides or bromides) to one or more fluid stream (e.g. a pulp fiber slurry), and then step (b) is practiced to detect the amount of marking chemical.

As earlier indicated, one of the best utilizations of the techniques according to the invention in a pulp and paper mill is with respect to black liquor. For example, step (a) may be practiced prior to entry of the black liquor into an evaporator, and step (c) practiced to control operation of the evaporator. Alternatively, the black liquor may be strong black liquor (after evaporation), so that step (a) is practiced just prior to entry of the black liquor into a recovery boiler, and step (c) is practiced by controlling operation of the recovery boiler, such as the primary and secondary air supplies. Alternatively, step (c) may be practiced to effect emergency shutoff of the black liquor feed in cases a suddenly elevated hydrogen/carbon ratio indicates an undesirable high water content in the black liquor feed. Such high water content could lead to a steam explosion if left uncontrolled. When black liquor is the fluid stream being analyzed, it has been found that when the liquor stream has a flow cross-sectional dimension of about 14–20 centimeters, particularly using the prompt gamma neutron activation analysis technique, the results are optimized. In such a situation, a germanium semi-conductor detector is typically used, shielded from a neutron emitter by about 2–3 centimeters of lead radiation shielding, or a sodium iodide (NaI) detector may be used.

While the invention is particularly useful for the analysis of black liquor, and subsequent control of black liquor handling steps, the invention is also applicable to determination of density of slurries. However rather than determining density or water content or consistency in a manner such as that of conventional gamma ray absorption devices (as disclosed in U.S. Pat. No. 4,239,590), according to the invention the amount of carbon in a slurry is analyzed. Alternatively the amount of many of the trace chemicals in the fibers in the slurry can be measured to use as a basis for density measurement, which then may be utilized to determine the precise solids consistency. Then the amount of treatment chemical added to the slurry may be controlled downstream, or the slurrying liquid/cellulose material ratio may be controlled upstream of where the analysis takes place.

The invention is capable of determining the amount of sulfur, sodium, calcium, chlorine, potassium, hydrogen, carbon, or combinations of these elements, in the fluid stream, and a common radiation source may be associated with a plurality of fluid streams (e.g. disposed in a circle therearound), with a plurality of detectors, one associated with each of the streams; or a single movable detector may be provided. Analysis takes place utilizing a computer.

According to another aspect of the present invention, a method of analyzing a fluid stream comprising a liquid with dissolved solids produced during the production or treatment of cellulose pulp, to determine the amount of one or more elements therein, is provided. The method comprises the following steps: (a) Causing the liquid with dissolved solids produced during the production or treatment of cellulose pulp to continuously flow in a first direction. (b) Directing radiation toward the flowing liquid (e.g. in a second direction, substantially perpendicular to the first direction), to bombard the solids in the liquid. (c) Detecting the radiation passing through or emanating from the flowing liquid as a result of step (b). (d) Converting the detected radiation to electrical signals. And, (e) analyzing the electrical signals with a computer to determine the amount of one or more elements present in the liquid.

Steps (c)-(e) may be practiced by detecting the radiation with a cryostatically cooled detector, or a suitable crystal material detector (e.g. an NaI detector), to produce a signal, modulating the signal emitted by the detector to a short step pulse without changing the amplitudes, converting the analog pulses into digital form, dividing the pulses according to their amplitudes into channels, and analyzing the multiple channels to form a spectrum.

According to yet a still further aspect of the present invention, an apparatus for analyzing pulp mill liquids is provided. The apparatus comprises: A neutron source. A conduit for the liquid to be analyzed, and having an interior cross-sectional dimension of about 14–20 centimeters. A detector mounted on the opposite side of the conduit from the gamma ray source. And, about 2–3 centimeters of lead radiation shielding provided between the detector and the neutron source.

According to still another embodiment of the invention, analysis apparatus is provided comprising the following elements, for performing multiple analyses at the same time and relatively inexpensively: A source of neutrons. A plurality of conduits each disposed in operative association with the source of neutrons. A gamma ray detector associated with each of the conduits, and disposed on the opposite side of each of the conduits from the neutron source, or a single detector that is manually or mechanically movable from one location to another. And, lead shielding operatively associated with each of the gamma ray detectors.

The invention also contemplates apparatus for analyzing elemental constituents of flowing fluent material, comprising the following components: A first, main conduit. Second and third branch conduits connected to the first conduit. The second conduit having an operative portion thereof with an interior flow path of about 2–6 centimeters. The third conduit having an operative portion thereof with an interior flow path greater than that of the second conduit. A neutron source (e.g. Californium) disposed in operative association with both the second and third conduit operative portions. And at least one detector associated with the second and third conduit operative portions for detecting gamma radiation or the like associated with the neutron source after bombardment of fluent material flowing through said conduits.

The invention also contemplates a method of determining one or more of at least the partial elemental makeup, concentrations of molecules, concentrations of chemical substances, distribution of flow, and whether chemicals are freely flowing or bound to pulp fibers, of a stream of cellulose pulp fibers slurry. The method comprises the steps of: (a) Making continuous on-line analysis of the stream by NMR (e.g. $^1$H-MR). (b) Determining (e.g. with a computer) desired features of the analysis; and (c) in response to (b), controlling one or more processes for acting on the stream to optimize the one or more processes.

It is the primary object of the present invention to provide for the effective analysis, and typically subsequent control, of processes and equipment in a cellulose pulp mill, by continuous on-line elemental analysis. This and other objects of the invention will become clear from an inspection of the detailed description of the invention, and from the appended claims.

DETAILED DESCRIPTION OF THE DRAWING

Figure 1:
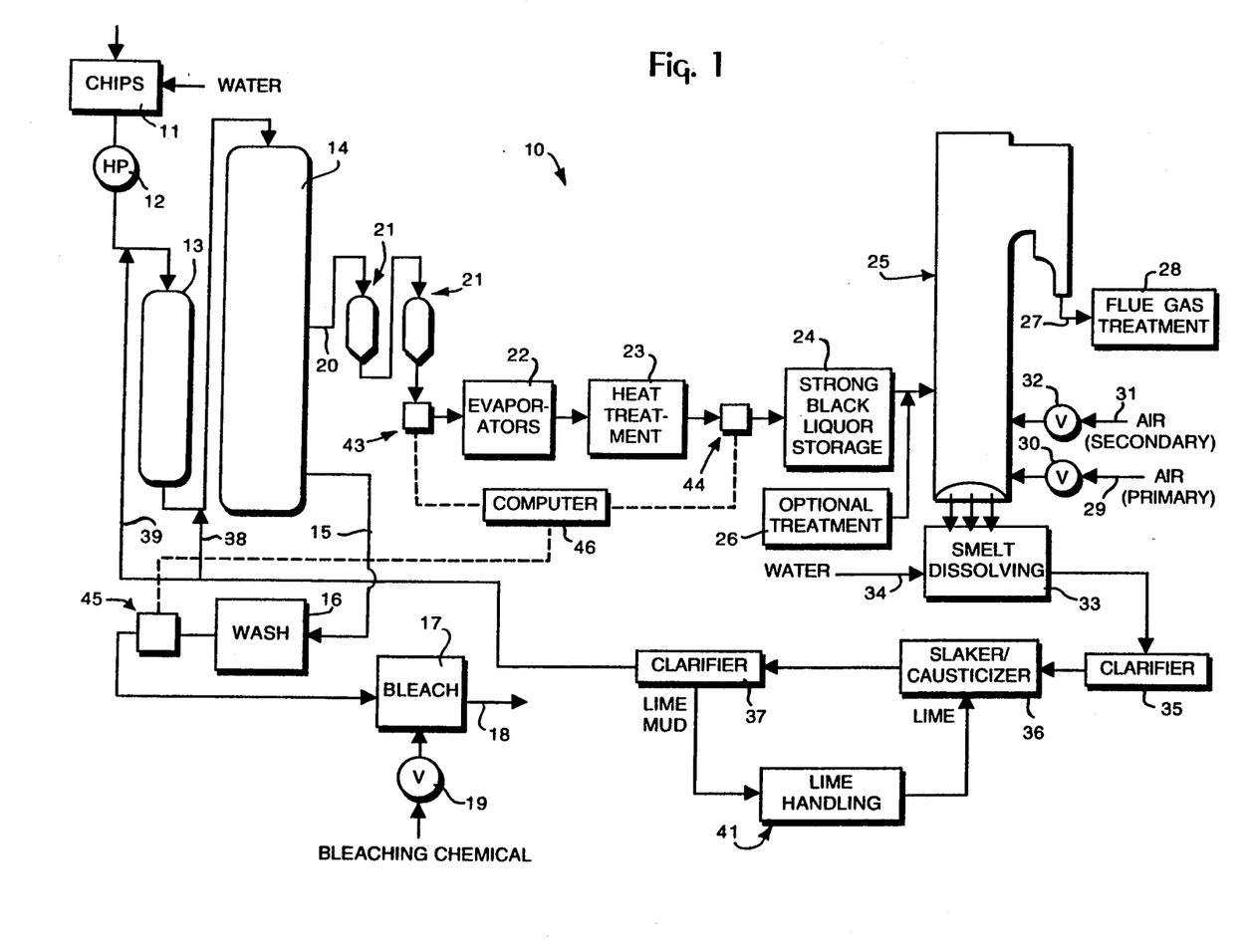
FIG. 1 is a schematic view showing exemplary apparatus for the production of paper pulp and recovery of chemicals, with which the invention may be utilized.

FIG. 1 schematically illustrates a number of conventional components of a conventional pulp mill 10. Typically, comminuted cellulosic fibrous material, such as wood chips, is combined with water in a device 11, such as a chips chute, in proper proportions, and then is transferred by a high pressure transfer device 12 to an impregnation vessel 13, and then to a continuous digester 14. Produced pulp is removed from the bottom of the digester 14 in line 15, washed as indicated schematically at 16, bleached as indicated schematically at 17, and otherwise acted upon to produce a final product in line 18. Bleaching chemical is added to the pulp in the bleach plant 17 via a plurality of valves, such as schematically illustrated by valve 19 in FIG. 1.

During the treatment of the pulp, it is highly desirable to recover the cooking chemical (white liquor in the case of kraft pulping). For this purpose, black liquor is typically continuously withdrawn through line 20 near the middle of the continuous digester 14, is flashed into steam in flash tanks 21, and then is led to a series of conventional evaporators 22. Heat treatment of the black liquor to reduce its viscosity and to drive off some of the sulfur may optionally be practiced as indicated at stage 23 in FIG. 1, utilizing the techniques as described in U.S. Pat. No. 4,929,307. The evaporator stages 22, and optionally heat treatment stage 23, produce a strong black liquor, having a high concentration of dissolved solids, which may be stored in a tank 24 and ultimately supplied as fuel to be burned in a conventional recovery boiler 25. Optional treatment—as indicated as 26 in FIG. 1—of the black liquor to remove undesirably high levels of some elements (such as chlorides) may be utilized just prior to the recovery boiler 25.

The recovery boiler 25 has flue gases which are discharged at 27 and treated at 28. Primary air, via line 29 and valve 30, and secondary air, via line 31 and valve 32, are provided to the recovery boiler 25 to effect combustion of the black liquor. The smelt formed adjacent the bottom of the recovery boiler 25 flows into a tank 33 where it is dissolved, by the addition of water from line 34, to produce green liquor, which is subsequently clarified at stage 35. Typically the clarified green liquor is slaked and then causticized, as indicated at stage 36, to produce white liquor, which is clarified as indicated at 37, and then fed via lines 38 and 39 to the cellulose material slurry being fed to the digester 14 and in the impregnation vessel 13, respectively. The lime for effecting causticization is handled as indicated schematically at 41 in FIG. 1.

According to the present invention, continuous on-line elemental analysis is utilized at various points throughout the pulp production facility 10. While in the exemplary embodiment illustrated in the drawings the on-line elemental analysis equipment is shown only in association with particular portions of the black liquor treatment system, it is to be understood that such techniques may be employed in many different places in the chemical recovery loop. Also, while continuous on-line elemental analysis is only illustrated at one point in the fiber line in the exemplary embodiment illustrated, it is to be understood that it may be utilized in many different points in the fiber line, to effect a number of different controls.

Figure 7:
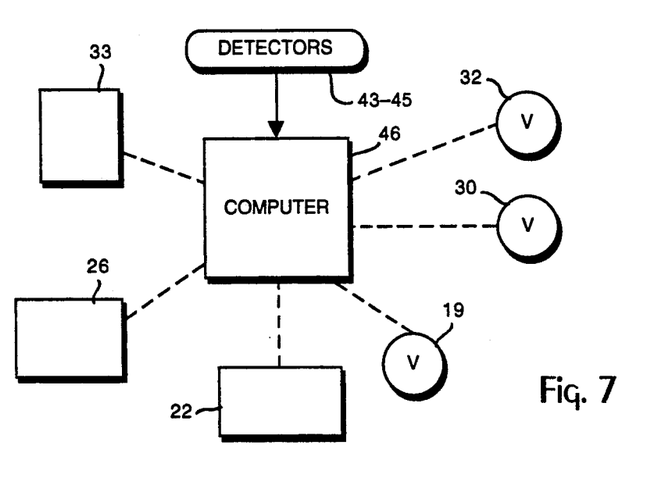
FIG. 7 is a control schematic illustrating various control components from a central computer, according to the invention.

FIG. 1 schematically illustrates continuous on-line elemental analyses units shown by reference numerals 43, 44, and 45 in FIG. 1, connected to a computer 46. Each of the units 43 through 45 is capable of determining the elemental composition of the liquid (whether its a liquid having dissolved solids, or a slurry with suspended comminuted cellulose material) with which it is associated. FIG. 7 schematically illustrates the control arrangement by which the computer 46 accepts data from the detectors associated with units 43-45, and then controls various components of the rest of the mill 10, such as the valves 19, 30 and 32, and the treatment stations 22 (evaporators), 26 (optional treatment to remove chemicals, such as excess chlorides, from the black liquor), and 33 (smelt dissolving tank).

It is noted that the analysis and determinations made according to the invention to control processes according to the invention (whether upstream or downstream, using feedback or feed forward) need not be completely accurate, nor instantaneous. In a pulp mill for all except a few analyzes (e.g. determination of hydrogen in water, with subsequent shut down as a process control, to prevent explosions) can easily accommodate a time delay of about 5-20 minutes (or more) between initial analysis at a point and subsequent process control, and the accuracy need only be in the range of roughly about 85-98% (that is 99+% accuracy, required in many prior art processes outside the pulp and paper field, is totally unnecessary). The length of measurement time can be adjusted, and the controls implemented can be automatic or manual.

Figure 2:
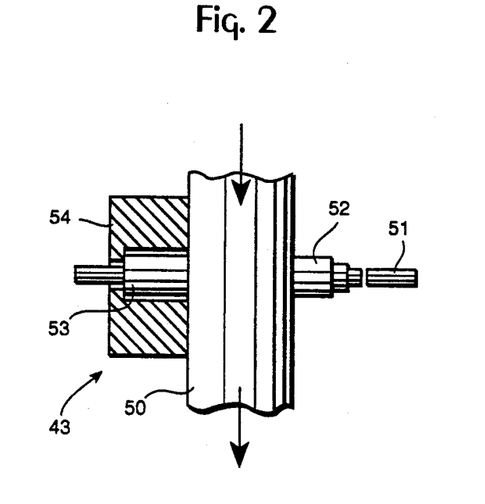
FIG. 2 is a side view, partly in cross-section and partly in elevation, of an exemplary analysis unit utilized in the practice of the invention.

An exemplary analysis unit is illustrated schematically at 43 in FIG. 2. The apparatus includes a conduit 50 through which the fluid stream being analyzed (in the case of the unit 43, black liquor) flows. On one side of the conduit 50 is a source of radiation, such a neutron source 51 (e.g. a 241 Americium-Beryllium source which has a half life of 433 years and remains stable in intensity within one percent for about 10 years), with an external gamma ray (lead) shielding 52, and on the opposite side is a detector 53, encased in lead shielding 54. The detector 53, particularly if prompt gamma neutron activation analysis is utilized, is preferably a coaxial germanium semi-conductor detector (often referred to as a "Ge-Li detector"). Alternatively a Californium 252 neutron source or a Sodium Iodide (NaI) detector may be used.

It has been found according to the invention that the thickness of the "sample" being analyzed is an important factor in the geometry of measurement, and it affects the optimum thickness of the lead shielding 52 that is utilized. For black liquor, it has been found that the sample thickness (that is the internal cross-sectional dimension) of the conduit 50 at which the components 51, 53 are disposed (on opposite sides) is about 14-20 centimeters, with the lead shielding 52 then about 2-3 centimeters thick. Of course the conduit 50 can merely be a conventional black liquor conduit, or where a typical conduit is much larger than 14-20 centimeters in diameter, conduit 50 may be a branch conduit which passes through the unit 43, and then back into the main black liquor conduit.

Figure 3:
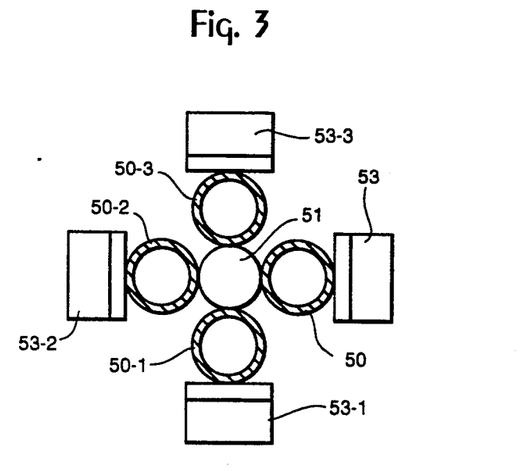
FIG. 3 is a schematic top view, partly in cross-section, of a form of apparatus according to the invention in which a common radiation source is utilized for a plurality of different fluid streams.

FIG. 3 illustrates an exemplary embodiment in which a single neutron source 51 is provided, associated with a plurality of conduits, such as conduits 50, 50-1, 50-2, and 50-3. Each of the conduits has its own detector associated therewith, such as the detectors 53, 53-1, 53-2, and 53-3, either with common lead shielding or with lead shielding for each of the detectors. In this way, costs can be minimized. One particularly good application for a system such as illustrated in FIG. 3 would be an analysis of the black liquor associated with the evaporators 22. A separate conduit 50, 50-1, etc. could be provided associated with each evaporator stage, such as a branch conduit from the inlet to each of the stages.

For the apparatus of FIG. 3, a modification may be provided. In the modification, only one detector 53 is provided, which is mounted so that it is movable (in a stepped manner) with respect to the conduits 50, 50-1, etc., analysis being performed on only one conduit at a time.

Figure 8:
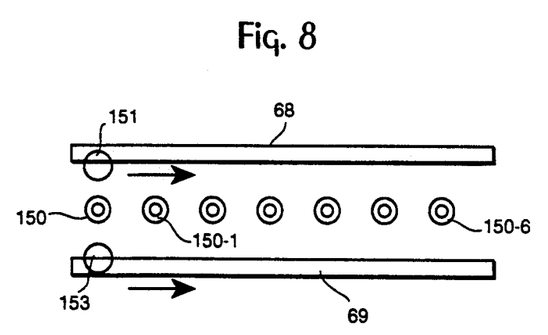
FIG. 8 is like that of FIG. 3 only showing a different configuration of conduits with a single movable neutron source and a single movable detector.

As seen in FIG. 8, where structures comparable to those in FIG. 3 are illustrated by a like reference numeral only preceded by a "1", a different arrangement between components is provided. In this case the neutron source 151 is movable (along track 68), as is the single detector 153 (along track 69). The source 151 and detector 153 are indexed from one conduit, e.g. 150, to the next, e.g. 150-1, to make an analysis of each conduit in sequence, and then may be moved back to the start by a motor, hydraulic or pneumatic actuator, or the like.

Figure 4:
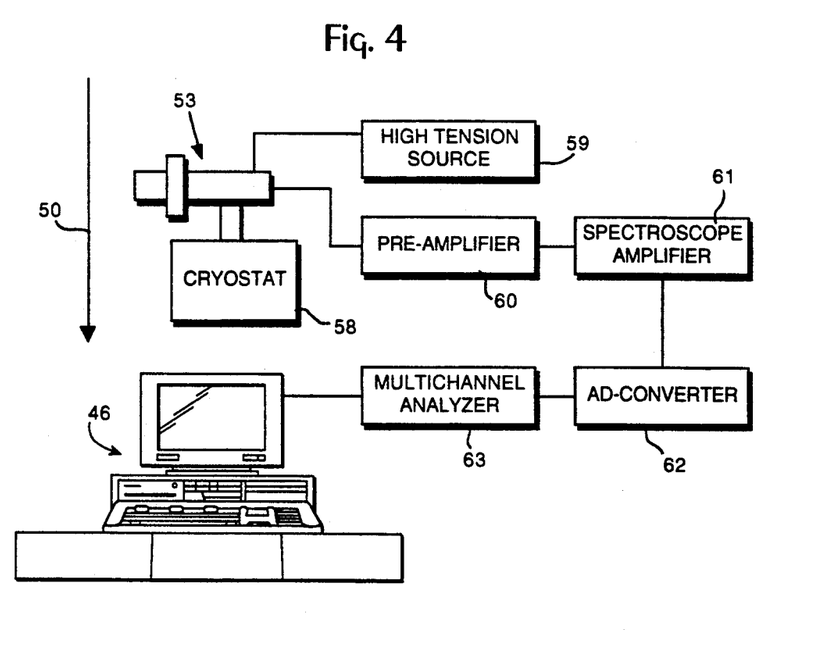
FIG. 4 is a schematic view showing various components for detecting and analyzing a particular quality of a pulp mill liquid.

FIG. 4 illustrates analyzing apparatus associated with a detector 53 for analyzing the output from the detector 53. As illustrated in FIG. 4, the Ge-Li detector may be cryostatically cooled to a temperature of about −200° C., utilizing cryostat 58, and the detector 53 is supplied from the high tension source 59. The output from the detector 53 is fed to preamplifier 60 which modulates the pulse emitted by the detector 53 to a short step pulse without changing the amplitudes. After the preamplifier 60 the signal is directed to a spectrascopic amplifier 61 and then further to an AD-converter 62 which converts the analog pulses into digital form. A multi-channel analyzer 63 divides the pulses from the AD-converter 62 according to their amplitudes into channels, from which they are read into the computer 46. In the computer 46 a multi-channel analyzer program forms the spectrum of elemental analysis and saves it for further processing.

Figure 5:
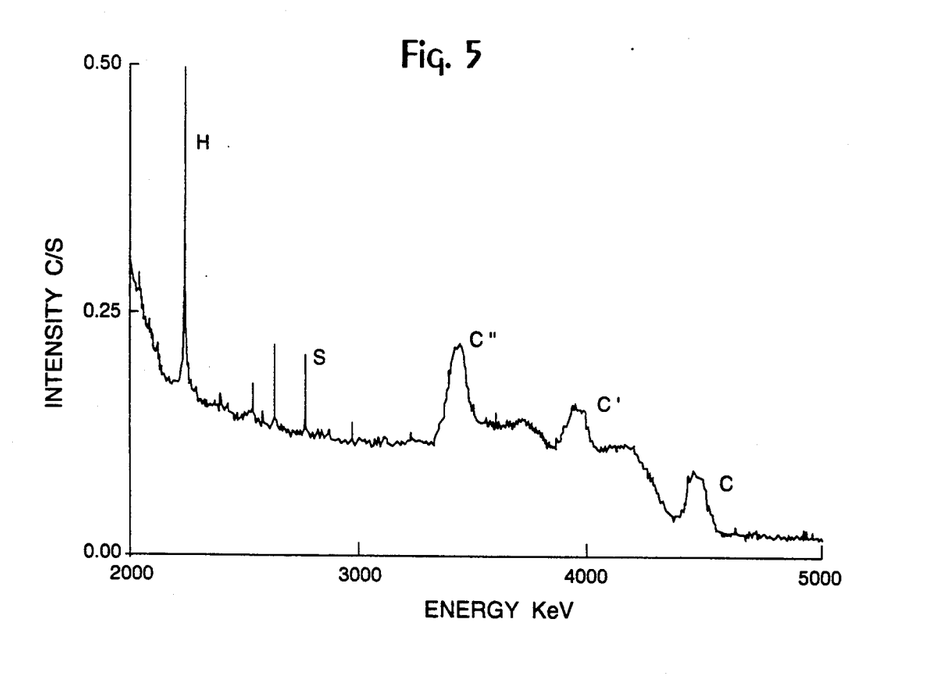
FIGS. 5 and 6 are graphical representations of results achieved from elemental analysis of black liquor, according to the present invention.
Figure 6:
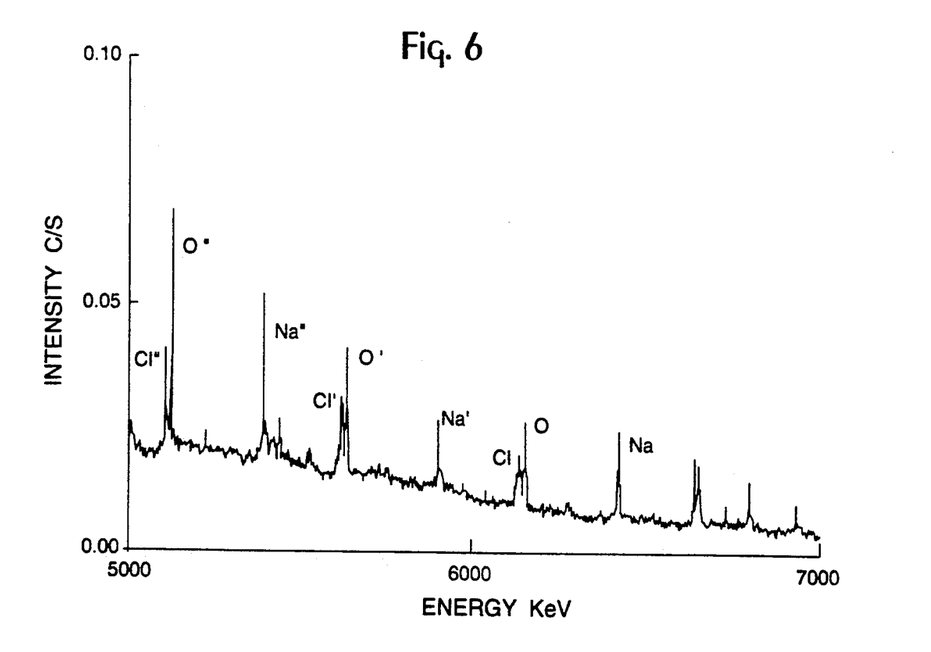

FIGS. 5 and 6 illustrate typical spectrum analysis for a number of different elements. FIG. 5 is from the Ge-Li detector 53 when an exemplary sample of black liquor was analyzed, utilizing 2,000-5,000 keV energy particles, while FIG. 6 is from the same sample of black liquor utilizing 5,000-8,000 keV particles.

In one particular analysis according to the present invention, black liquor was analyzed utilizing a neutron source 51 and a Ge-Li detector 53, performing prompt gamma neutron activation analysis. The results of the elemental analysis as utilizing that equipment is as follows (the margin of error in parentheses after each element):

TABLE I

| | Elemental Intens. (c/s) GeLi |
|---|---|
| H | 9.8 (±0.5%) |
| S | 0.7 (±5%) |
| C | 5% |
| O | 0.13 (±15%) |
| Cl | 0.22 (±10%) |
| O + Cl | — |
| Na | 0.42 (±6%) |

Utilizing the elemental analysis set forth above, a number of control scenarios may be implemented. For example, if the black liquor analyzed is strong black liquor, the analysis taking place prior to combustion in the recovery boiler 25, the heat value of the black liquor may be calculated from the relative amounts of carbon, hydrogen, oxygen, and other substances in the analysis in Table I, utilizing the computer 46. Then the control of the total combustion air (as by controlling valves 30, 32) can be effected so as to optimize combustion, such as making the rate of reduction high and the emissions of harmful and sooty flue gases low. Also, on the basis of the Na/S ratio, both the sulfur emissions from the recovery boiler 25 and the sulfidity of the smelt fed to tank 33 can be controlled. Further, it is possible to adjust the distribution of air to the recovery boiler 25 on the basis of the Na/S ratio, which also optimizes reduction and emissions. By determining the content of chloride and other harmful substances, the concentration of those substances can be monitored and removed as necessary, e.g. utilizing an optional treatment stage 26 (e.g. for chloride removal).

The techniques according to the present invention may be used for the determination of the amounts, and relative amounts, of sulfur, sodium, calcium, chlorine, carbon, hydrogen, oxygen, potassium, or combinations thereof. A rapid increase in the percentage of hydrogen would warn of a water leak into the black liquor, that is probably from a malfunction of the evaporators 22, which then could be repaired before a major disturbance or a steam explosion occurred in the recovery boiler 25. If one determines the dry solids content of black liquor flowing through an evaporator 22 then the evaporator 22 can be controlled and monitored more effectively. Neutron activation analysis can provide ratios of the chemicals, including hydrogen, for a straight-forward determination of a dry solids content without the necessity for taking samples.

When the invention is utilized for determining consistency of a pulp flow (e.g. at 45 in FIG. 1), the calculation of consistency is determined from a direct measurement of the carbon content and hydrogen content of the flow therethrough. This information then is used to directly control processing of the pulp at various stages of the fiber line, such as by controlling the amount of bleaching chemical added in the bleach plant 17 via valves 19.

Determination of carbon in a sample is typically effected in a different manner than determination of many other elements. Carbon measurement is based on the 4.33 MeV gamma radiation. An Americium-Beryllium neutron source also emits gamma radiation of about this energy level, thereof it is best to place radiation shielding between the neutron source and the sample, or to use a Californium 252 neutron source, which emits almost no disturbing gamma rays of the same energy. For fast neutron detection, the optimum sample thickness is only a few centimeters, e.g. about 2-6 centimeters, because neutrons thermalize very rapidly in sample material (e.g. a pulp slurry) because of a high percentage of light nuclei.

Figure 9:
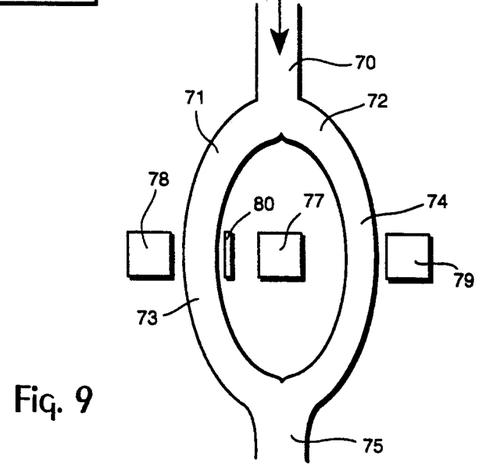
FIG. 9 is a schematic view showing an apparatus configuration according to the invention in which carbon analysis is made using one detector, and analysis of other elements using another detector.

An optimum way to practice the invention when carbon is one of the elements whose content is to be determined is possible utilizing the apparatus of FIG. 9. In this embodiment, a first, main conduit 70 branches into second and third conduits 71, 72 respectively, which may recombine at 75 if desired. Each conduit 71, 72 has an operative portion—73, 74 respectively—associated with stationary neutron source 77 (e.g. Californium). The portion 73 preferably is a flat conduit portion having an inside thickness of only about 2-6 centimeters, through which the pulp fiber slurry flows. The portion 74 has much larger thickness than the portion 73, e.g. a round configuration with a diameter of about 12-15 centimeters. The detector 78 associated with portion 73 is for carbon, while the detector 79 associated with portion 74 is for other elements. Particularly if the source 77 is an Americium-Beryllium source, radiation shielding 80 may be provided between source 77 and portion 73.

The invention can be practiced by making an elemental analysis of trace materials that are inherent (naturally occurring) in the fluent material (e.g. if the source of trace materials, such as magnesium, in a species of wood from a certain location is known, magnesium can be detected in a pulp slurry made from that wood species), or a marking chemical can be used, and the amount of marking chemical analyzed. For example, for pulp slurries chlorides or bromides may be added as a marking chemical, and they will attach to the pulp fibers. The amount of chlorides or bromides attached to the wood fibers may then be determined.

It should be understood that while the invention has been described specifically with respect to prompt gamma neutron activation analysis, it is understood that it is also applicable to other techniques, such as NMR, particularly 'H-MR, proton activation analysis, and X-ray fluorescence. Using NMR provides benefits in addition to making elemental analysis, as described earlier.

It will thus be seen that according to the present invention an effective mechanism for controlling equipment used in the processing of cellulose pulp, and the recovery of chemicals during the production of chemical pulps, as well as advantageous analyzing techniques, and associated apparatus, have been provided. While the invention has been herein shown and described in what is presently conceived to be the most practical and preferred embodiment it will be apparent to those of ordinary skill in the art that many modifications may be made thereof within the scope of the invention, which scope is to be accorded the broadest interpretation of the appended claims so as to encompass all equivalent structures and processes.

What is claimed is:

1. A method of effecting process control of equipment used for the production of cellulose pulp, comprising the steps of:
   (a) making continuous on-line analysis of one or more of the partial elemental makeup, concentrations of molecules, and concentrations of chemical substances of one or more fluid streams selected from the group consisting of black liquor and liquid slurries including at least about 3% comminuted cellulosic fibrous material by bombarding the fluid stream being analyzed with radioactive particles or radiation, and detecting radioactive particles or radiation as a result of that bombardment;
   (b) determining one or more of at least the partial elemental makeup, concentrations of molecules, and concentrations of chemical substances of the one or more fluid streams; and
   (c) in response to (b), controlling one or more processes for acting on the one or more fluid streams to optimize the one or more processes.

2. A method as recited in claim 1 wherein step (a) is practiced by prompt gamma neutron activation analysis.

3. A method as recited in claim 1 wherein steps (a) and (b) are practiced to a level of accuracy of about 85-98%, and wherein step (c) is practiced after a time delay from step (a) of about 5-20 minutes.

4. A method as recited in claim 1 wherein steps (a) and (b) are practiced to determine the amount of sulfur, sodium, potassium, calcium, chlorine, hydrogen, oxygen, carbon, combinations thereof, or chemical compounds containing them, in the fluid stream.

5. A method as recited in claim 1 comprising the further step (d), prior to step (a), of adding a marking chemical to one or more fluid streams, and wherein step (b) is practiced to detect the amount of marking chemical.

6. A method as recited in claim 1 wherein the fluid stream being analyzed is black liquor, and wherein step (a) is practiced prior to entry of the black liquor into an evaporator and wherein step (c) is practiced by controlling operation of the evaporator.

7. A method as recited in claim 1 wherein the fluid stream being analyzed is strong black liquor, and wherein step (a) is practiced prior to entry of the black liquor into a recovery boiler, and wherein step (c) is practiced by controlling operation of the recovery boiler.

8. A method as recited in claim 7 wherein step (c) is further practiced by controlling the flow of primary and secondary air to the recovery boiler.

9. A method as recited in claim 1 wherein the fluid stream being analyzed is black liquor, and wherein step (a) is practiced by prompt gamma neutron activation analysis of a black liquor stream having a flow cross-sectional dimension of about 14-20 cm.

10. A method as recited in claim 9 wherein step (a) is practiced utilizing a germanium semiconductor detector shielded from a neutron emitter by about 2-3 cm of lead radiation shielding, and by disposing the detector on the opposite side of the black liquor stream flow cross-section of about 14-20 cm from the emitter.

11. A method as recited in claim 10 wherein step (a) is further practiced by emitting neutrons from a 241 Americium-Beryllium source.

12. A method as recited in claim 10 wherein step (a) is further practiced by emitting neutrons from a Californium 252 source.

13. A method as recited in claim 9 wherein the fluid stream being analyzed is strong black liquor, and wherein step (a) is practiced prior to entry of the black liquor into a recovery boiler, and wherein step (c) is practiced by controlling operation of the recovery boiler.

14. A method as recited in claim 9 wherein step (a) is practiced prior to entry of the black liquor into an evaporator, and wherein step (c) is practiced by controlling operation of the evaporator.

15. A method as recited in claim 1 wherein the fluid stream being analyzed is a slurry of comminuted cellulose material in liquid having a solids consistency of about 3-20%; and wherein steps (a) and (b) are practiced by analyzing the carbon content of the slurry to determine its precise solids consistency, or trace element content, or fibers.

16. A method as recited in claim 15 wherein step (c) is practiced by controlling the amount of treatment chemical added to the slurry downstream of where step (a) is practiced.

17. A method as recited in claim 15 comprising the further step of controlling process steps upstream of where step (a) is practiced.

18. A method as recited in claim 15 wherein step (c) is practiced by controlling the slurrying liquid/cellulose material ratio upstream of where step (a) is practiced.

19. A method as recited in claim 1 wherein step (a) is further practiced by using a common radiation source, a plurality of fluid streams, and at least one detector constructed so that a detector may be associated with each of the plurality of streams.

20. A method as recited in claim 1 wherein step (b) is practiced utilizing a computer.

21. A method as recited in claim 1 comprising the further step (d), prior to step (a), of adding a marking chemical to one or more fluid streams, and wherein step (b) is practiced to detect the amount of marking chemical.

22. A method as recited in claim 21 wherein the fluid stream being analyzed is a slurry of comminuted cellulose fibers in liquid having a solids consistency of about 3% or more; and wherein step (d) is practiced by adding a chemical capable of marking the cellulose fibers, and wherein step (b) is practiced to detect the amount of marking chemical on fibers.

23. A method as recited in claim 22 wherein step (d) is practiced by adding a chemical selected from the group consisting of bromides and chlorides to mark the fibers.

24. A method as recited in claim 1 wherein steps (a) and (b) are practiced by bombarding the fluid streams with neutrons to detect carbon atoms in a first fluid stream about 2-6 centimeters thick utilizing a first detector, and to detect other elements in a second fluid stream thicker than the first fluid stream utilizing a second detector.

25. A method as recited in claim 24 wherein the first and second fluid streams have substantially the same composition, being branches from a main fluid stream; and wherein step (a) is practiced utilizing Californium as a source of neutrons.

* * * * *